(12) United States Patent
Blackdiamond

(10) Patent No.: US 10,591,138 B1
(45) Date of Patent: Mar. 17, 2020

(54) CONTAINER WITH INTERNAL ILLUMINATION SOURCE

(71) Applicant: Michael Nigel Blackdiamond, Napa, CA (US)

(72) Inventor: Michael Nigel Blackdiamond, Napa, CA (US)

(*) Notice: Subject to any disclaimer, the term of this patent is extended or adjusted under 35 U.S.C. 154(b) by 0 days.

(21) Appl. No.: 15/011,528

(22) Filed: Jan. 30, 2016

(51) Int. Cl.

| | | |
|---|---|---|
| *B01F 13/00* | (2006.01) | |
| *F21V 9/30* | (2018.01) | |
| *B65D 35/02* | (2006.01) | |
| *B65D 35/44* | (2006.01) | |
| *A61K 8/92* | (2006.01) | |
| *A61Q 19/00* | (2006.01) | |
| *A61Q 1/02* | (2006.01) | |
| *A61K 8/02* | (2006.01) | |
| *B01F 15/06* | (2006.01) | |
| *B01F 15/00* | (2006.01) | |
| *B01F 7/16* | (2006.01) | |
| *F21V 33/00* | (2006.01) | |
| *F21Y 101/02* | (2006.01) | |

(52) U.S. Cl.
CPC .............. *F21V 9/30* (2018.02); *A61K 8/0216* (2013.01); *A61K 8/92* (2013.01); *A61Q 1/02* (2013.01); *A61Q 19/007* (2013.01); *B01F 7/16* (2013.01); *B01F 15/00538* (2013.01); *B01F 15/06* (2013.01); *B65D 35/02* (2013.01); *B65D 35/44* (2013.01); *F21V 33/004* (2013.01); *A61K 2800/434* (2013.01); *B01F 2015/062* (2013.01); *F21Y 2101/02* (2013.01)

(58) Field of Classification Search
CPC .. A61K 2800/434; A61K 8/0216; A61K 8/92; A61Q 1/02; A61Q 19/007; B01F 15/00538; B01F 15/06; B01F 7/16; B01F 2015/062; F21V 33/004; F21V 9/16; F21Y 2101/02; B65D 35/02; B65D 35/44
See application file for complete search history.

(56) References Cited

U.S. PATENT DOCUMENTS

| | | | | |
|---|---|---|---|---|
| 2,745,947 | A | | 5/1956 | Sansous |
| 2,765,481 | A | * | 10/1956 | Manhart ................. B63B 51/04 362/158 |
| 4,209,259 | A | * | 6/1980 | Rains .................. B01F 13/0827 366/273 |
| 4,344,113 | A | | 8/1982 | Ditto |
| 4,490,931 | A | * | 1/1985 | Fleemin ................. G09B 23/00 40/406 |
| 4,700,871 | A | * | 10/1987 | Matsuo ..................... A61J 1/05 222/107 |
| 4,827,642 | A | * | 5/1989 | Chatten ................... G09F 19/02 40/426 |
| 4,913,555 | A | * | 4/1990 | Maeda ...................... A23G 9/12 261/DIG. 16 |
| 4,922,355 | A | * | 5/1990 | Dietz .................. A47G 19/2227 362/101 |

(Continued)

FOREIGN PATENT DOCUMENTS

WO  WO 2009007238  6/2008

*Primary Examiner* — David P Angwin
*Assistant Examiner* — Bob Zadeh
(74) *Attorney, Agent, or Firm* — Banner & Witcoff, Ltd.

(57) ABSTRACT

A fluid container and dispenser have an associated source of power to energize a light source coupled in optical communication with portion of the container to energize the luminescent fluid contents before they are dispensed.

2 Claims, 10 Drawing Sheets

(56) References Cited

U.S. PATENT DOCUMENTS

| | | | |
|---|---|---|---|
| 5,141,327 A * | 8/1992 | Shiobara | B01F 13/0827 366/127 |
| 5,586,823 A * | 12/1996 | Carr | B01F 13/0818 366/274 |
| 5,743,620 A * | 4/1998 | Rojas | A47G 19/2227 215/386 |
| 5,785,407 A | 7/1998 | Ratcliffe | |
| 6,065,848 A | 5/2000 | Tucker | |
| 6,163,248 A * | 12/2000 | Paek | A47G 19/2227 340/321 |
| 6,241,359 B1 * | 6/2001 | Lin | F21S 10/002 362/101 |
| 6,254,247 B1 * | 7/2001 | Carson | A47G 19/2227 359/32 |
| 6,305,817 B1 | 10/2001 | Johnston | |
| 6,352,352 B1 * | 3/2002 | Schletterer | A47G 19/2227 320/167 |
| 6,371,624 B1 | 4/2002 | Dorney | |
| 6,443,589 B1 * | 9/2002 | Lee | A47G 19/2227 362/101 |
| 6,508,022 B2 * | 1/2003 | Huang | G09F 19/08 40/406 |
| 6,592,007 B2 * | 7/2003 | Ho | B05B 11/0005 222/113 |
| 6,793,362 B2 * | 9/2004 | Tai | A47G 19/2227 362/101 |
| 6,793,363 B2 * | 9/2004 | Jensen | A47G 23/0309 362/101 |
| 7,018,062 B2 * | 3/2006 | Taylor | A47G 19/2227 362/101 |
| 7,258,458 B2 * | 8/2007 | Mochiachvili | A47G 23/0309 362/101 |
| 7,401,935 B2 * | 7/2008 | VanderSchuit | F21V 33/0028 362/101 |
| 7,419,072 B1 * | 9/2008 | Vanella | A47G 23/0309 222/113 |
| 7,434,983 B2 * | 10/2008 | Terentiev | B01F 7/00908 366/273 |
| 7,690,533 B2 * | 4/2010 | Stilley | B05B 1/00 222/113 |
| 7,695,186 B2 * | 4/2010 | Terentiev | B01F 7/00908 366/273 |
| 7,762,716 B2 * | 7/2010 | Terentiev | B01F 7/162 366/273 |
| 7,832,922 B2 * | 11/2010 | Schoeb | B01F 7/00716 366/273 |
| 8,690,418 B2 * | 4/2014 | Ludwig | B01F 3/04269 366/102 |
| 9,565,970 B2 * | 2/2017 | Alet Vidal | A47J 36/165 |
| 9,873,097 B1 * | 1/2018 | Dushine | B01F 13/0818 |
| 2002/0047024 A1 * | 4/2002 | Ho | B05B 11/0005 222/113 |
| 2003/0067764 A1 * | 4/2003 | Lau Ting Yup | G09F 13/24 362/84 |
| 2005/0073833 A1 * | 4/2005 | VanderSchuit | A47G 19/2222 362/101 |
| 2005/0180146 A1 * | 8/2005 | VanderSchuit | F21S 10/06 362/367 |
| 2006/0139928 A1 * | 6/2006 | Griffiths | B65D 51/248 362/276 |
| 2007/0007304 A1 * | 1/2007 | Bitton | F21S 10/002 222/113 |
| 2008/0057089 A1 | 3/2008 | Molina | |
| 2009/0166378 A1 * | 7/2009 | Stilley | B05B 11/0005 222/39 |

* cited by examiner

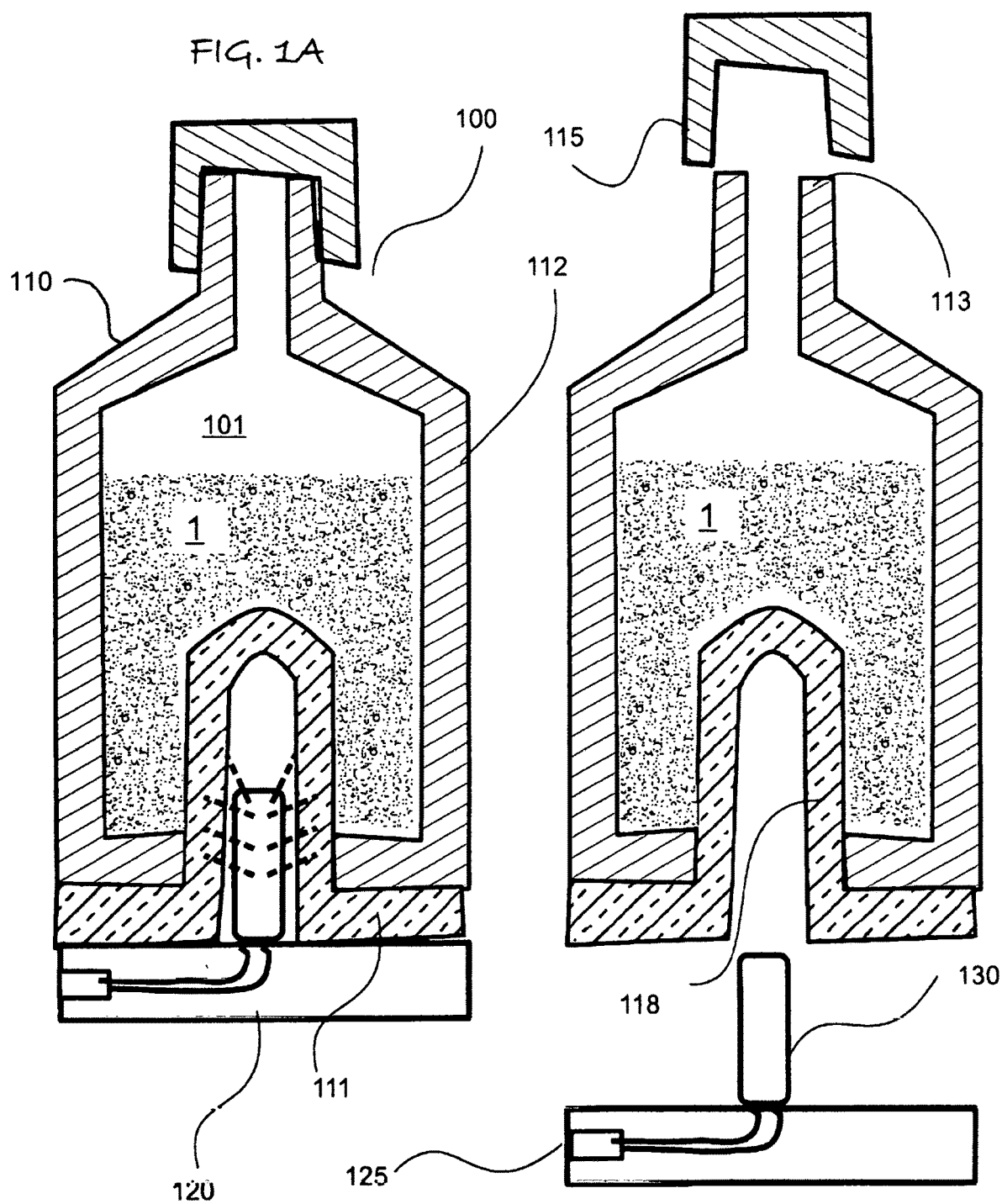

FIG. 3A
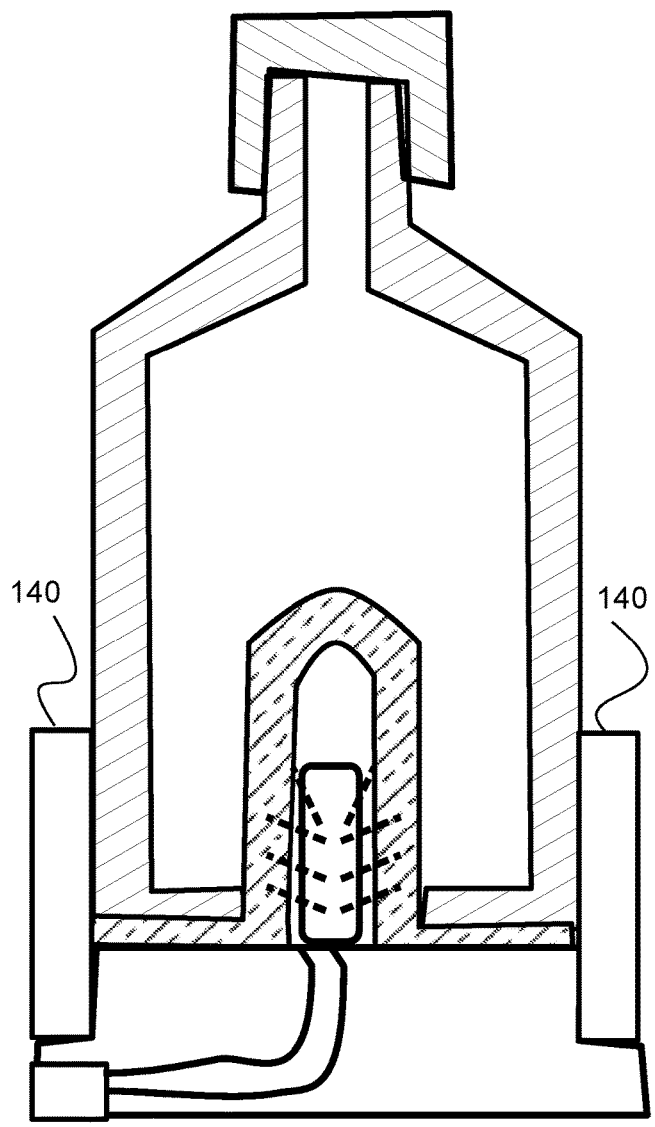
140   140
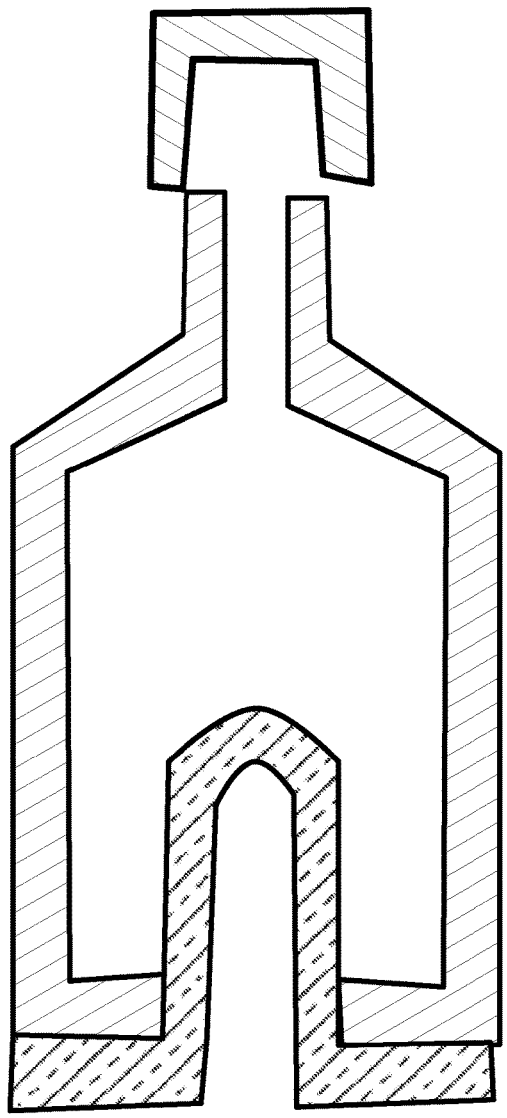
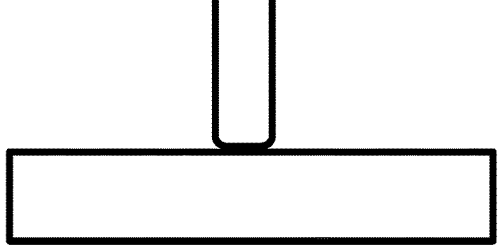
FIG. 3B

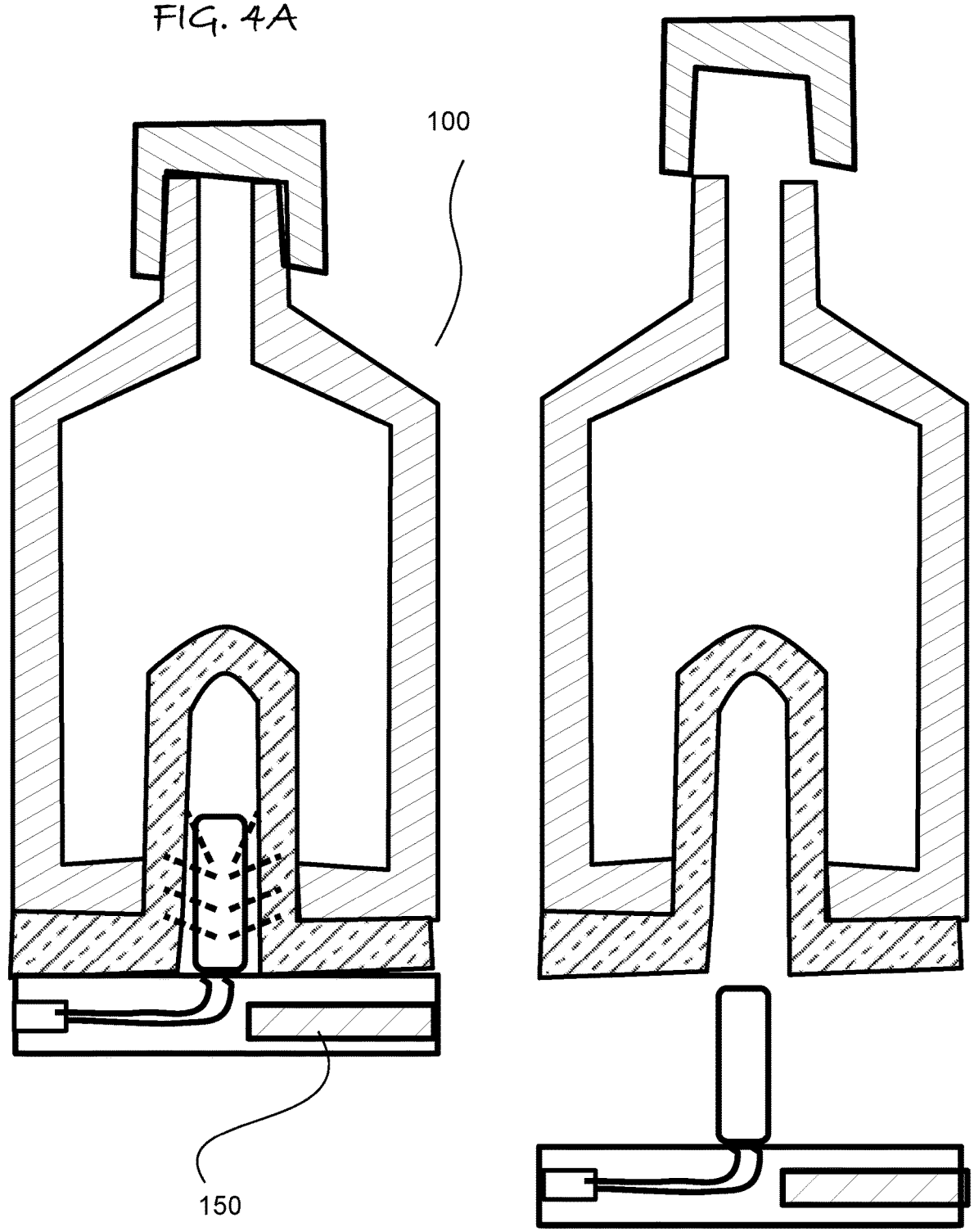

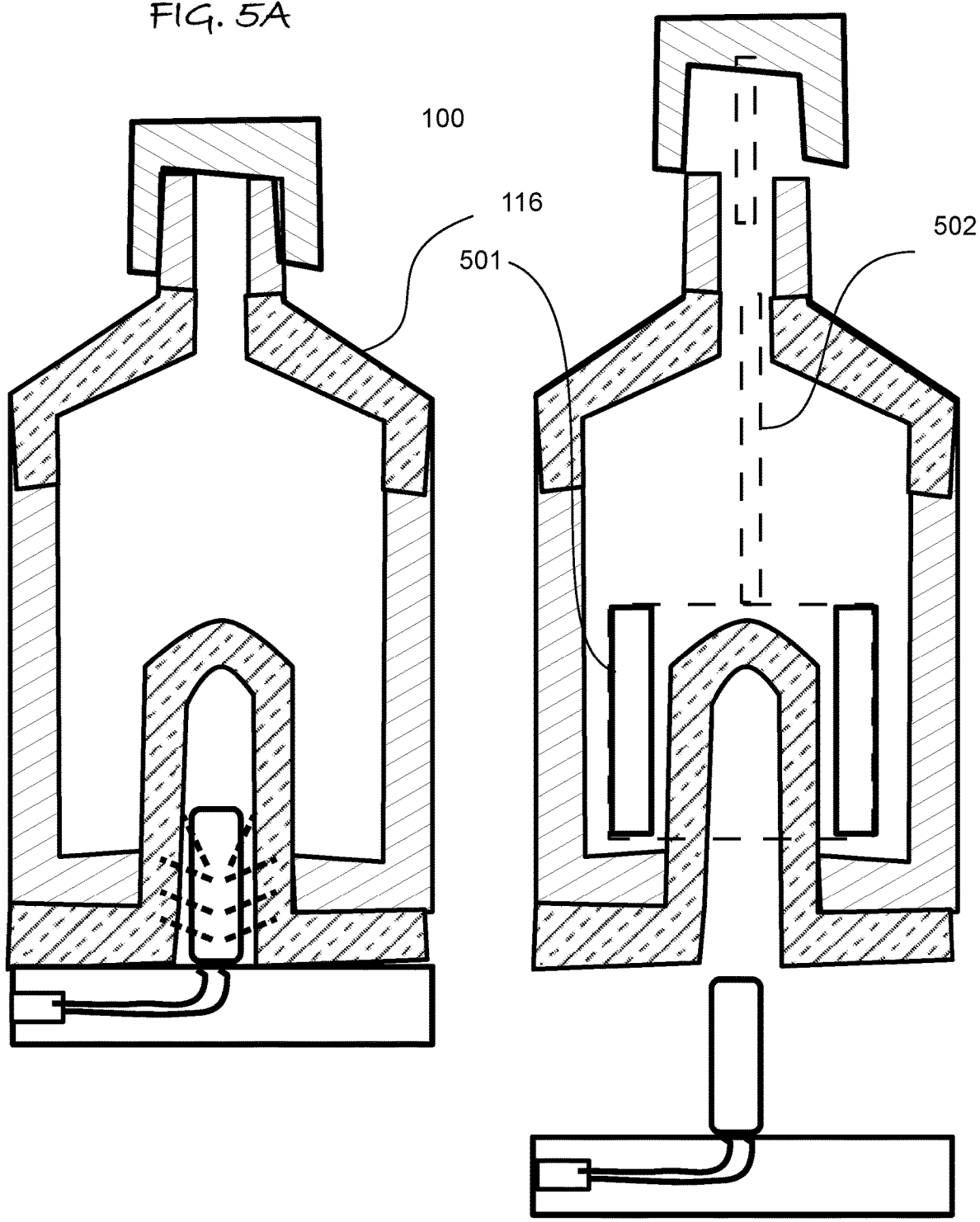

CONTAINER WITH INTERNAL ILLUMINATION SOURCE

CROSS REFERENCE TO RELATED APPLICATIONS

The present application claims the benefit of priority to the U.S. provisional patent application that was filed on Dec. 1, 2015, having Ser. No. 62/085,975, which is incorporated herein by reference.

A petition under 37 CFR1.78 (b) is being filed herewith to restore the right of priority to the above claim.

BACKGROUND OF INVENTION

The field of the invention is the storage and dispensing of fluid, which may be personal care products, such as creams, lotions or gels and related fluids for topical application, as well as body paints for fashion and entertainment, and in particular containers for the same.

Light emitting personal lubricant are disclosed in the US patent application having application serial number US2008/0057089 A1, which published on Mar. 6, 2008, which is incorporated herein by reference.

However, the luminescent properties of such products depend on exposure to a light source after they are applied to a person. Thus, the area of application may not be visible until the light source is applied, and then lighting is extinguished to see where the material has been applied.

Alternatively, the area of application may be visible in the substantial absence of visible light, provided UV or near UV light, such as "black light" are deployed. However, depending on the luminescent properties of the fluid, the light emission might not occur immediately as the fluid is applied.

It would be advantageous to overcome the above limitations.

The above and other objects, effects, features, and advantages of the present invention will become more apparent from the following description of the embodiments thereof taken in conjunction with the accompanying drawings

SUMMARY OF INVENTION

In the one aspect of the present invention, a first object is achieved by providing a fluid dispenser comprising a container having a bottom portion, substantially upright side wall surrounding the bottom portion which terminate at an upper rim, and a cap removably connected to an upper portion of the container, wherein the portions of the container between the bottom portion and sidewalls defines a cavity for confining a fluid, a transparent inner annulus that extends upward from the bottom portion of the container at least partly upward into said cavity, a means to connect an illuminating base to the bottom of the container so as to dispose a light source in optical communication within the inner annulus to irradiate fluid contents within the cavity.

A second aspect of the invention is characterized by such a fluid dispenser wherein the illuminating base further comprises a heating element that is disposed in thermal communication with one of the bottom and a lower portion of the sidewalls of the container when the light sources disposed within the inner annulus.

Another aspect of the invention is characterized by any such fluid dispenser wherein the illuminating base further comprises an external socket for receiving a power connection, were in the external socket is wired to one or more of the light source and the heating element Another aspect of the invention is characterized by any such fluid dispenser wherein the lighting element is a light emitting diode (LED)

Another aspect of the invention is characterized by any such fluid dispenser wherein the light emitting diode emits blue light.

Another aspect of the invention is characterized by any such fluid dispenser wherein the illuminating base is removably attachable to the bottom of the container with a least one of a snap, bayonet or screwed fitting.

Another aspect of the invention is characterized by any such fluid dispenser wherein the sidewalls of the container our deformable to squeeze fluid from the container.

Another aspect of the invention is characterized by any such fluid dispenser wherein the fluid dispenser further comprises a fluid having dispersed or dissolved luminescent material therein at least partially filling the container.

Another aspect of the invention is characterized a fluid dispenser comprising a container having a bottom portion, substantially upright side walls surrounding the bottom portion which terminate at an upper rim, and a cap removably connected to an upper portion of the container, wherein the portions of the container between the bottom portion and sidewalls defines a cavity for confining a fluid, wherein at least one of the bottom and a portion of the substantially upright walls are transparent, a means to connect an illuminating base to the bottom of the container so as to dispose a light source in optical communication to irradiate contents within the cavity.

Another aspect of the invention is characterized by any such a fluid dispenser wherein the illuminating base is removably connected to the bottom of the container so as to dispose a light source in optical communication with at least one of the bottoms and a portion of the substantially upright walls.

Another aspect of the invention is characterized by any such a fluid dispenser wherein the illuminating bases comprises a plurality of light sources for illuminating the substantially upright walls of the contains and at least a part of the illuminated portions of the upright walls are covered by an external reflector to re-direct light toward the cavity.

Another aspect of the invention is characterized by any such a fluid dispenser wherein the cavity contains a luminescent fluid.

Another aspect of the invention is characterized by any such a fluid dispenser wherein the container further comprises an at least partially transparent inner annulus that is in optical communication with one or more light sources of the illuminating base to irradiate fluid contents within the cavity that surround the inner annulus.

Another aspect of the invention is characterized by any such a fluid dispenser wherein a light source extends upward into the inner annulus.

Another aspect of the invention is characterized by any such a fluid dispenser wherein the at least partially transparent inner annulus has a central metallic reflector and is illuminated from below by an attached light source or a light source disposed in the base.

Another aspect of the invention is characterized by any such a fluid dispenser wherein the base further comprises at least one of a battery, transceiver, transmitter, controller, heater, thermal sensor and display.

Another aspect of the invention is characterized by any such a fluid dispenser wherein the base further comprises at least one of a controller and display in which the controller is operative to activate the display to indicate when the contents are at least one of ready for use, should be stirred or mixed, should be allowed to heat or be illuminated further.

The above and other objects, effects, features, and advantages of the present invention will become more apparent from the following description of the embodiments thereof taken in conjunction with the accompanying drawings.

BRIEF DESCRIPTION OF DRAWINGS

FIG. 1A is a cross-sectional elevation view of a first embodiment of the invention, in which FIG. 1B shows the components thereof separated for a method of use.

FIG. 2A is a cross-sectional elevation view of a first embodiment of the invention, in which

FIG. 3A is a cross-sectional elevation view of a third embodiment of the invention, in which FIG. 3B shows the components thereof separated for a method of use.

FIG. 4A is a cross-sectional elevation view of a fourth embodiment of the invention, in which FIG. 4B shows the components thereof separated for a method of use.

FIG. 5A is a cross-sectional elevation view of a fifth embodiment of the invention, in which FIG. 5B shows the components thereof separated for a method of use.

DETAILED DESCRIPTION

Figure 2A:
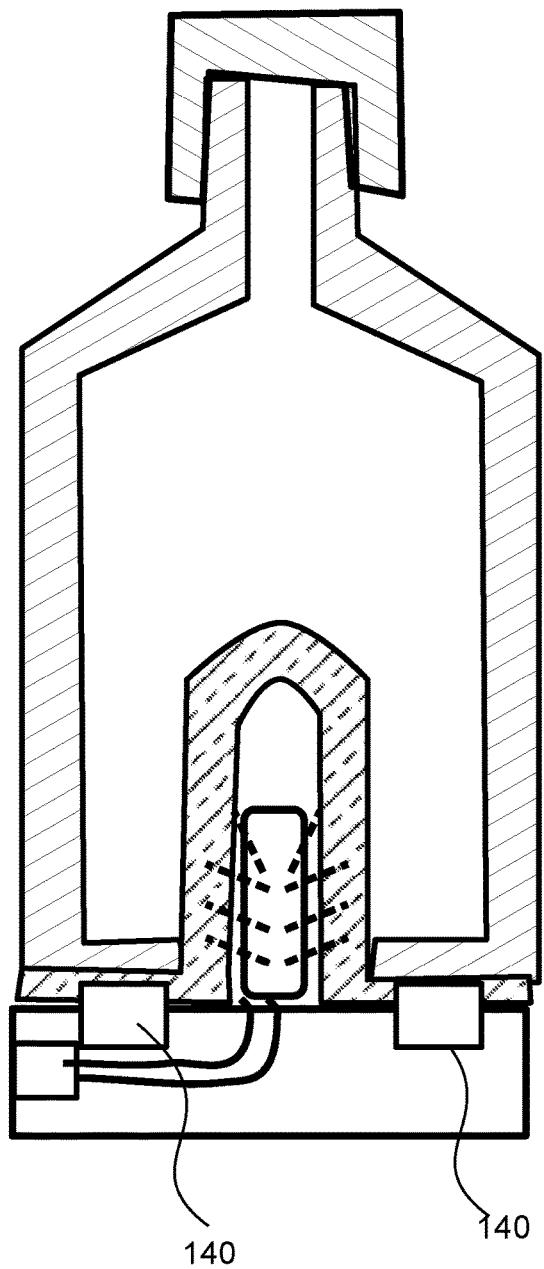

Referring to FIGS. 1A through 9, wherein like reference numerals refer to like components in the various views, there is illustrated therein a new and improved Container with Illumination Source, generally denominated 100 herein.

In one aspect, the aforementioned limitation to luminescent products for topical application is overcome by storage in a dispensing container having an integrated light source and means to energize the light source.

Such a container 100 as depicted in FIG. 1A-1B is a fluid dispenser which generally comprises a container 110 having a bottom portion 111 connected to side walls 112 that surround the bottom portion and then extend substantially upward to terminate at an upper rim 113. A cap or closure device 115 is removably connected to an upper portion of the container to form a fluid resistant seal at the rim 113. The portions of the container 110 between the bottom portion 111 and sidewalls 112 defines a cavity 101 for confining a fluid 1 that is to be dispensed either at the rim 113, such as when the cap 115 is removed, or opened at sealable opening within the cap 115, such as a pouring spout or spray nozzle, and the like.

In the various other embodiments there are several alternative and not mutually exclusive means to connect an illuminating base 120 to the bottom 111 of the container 110 so as to dispose a light source 130 in optical communication with the fluid 1 contents having a luminescent property that are stored in the cavity. It is the object of the invention to enable the illumination of the fluid contents such that they are luminescent when being dispensed via the cap 115.

In the embodiment of FIG. 1A-5B, a transparent inner annulus 118 that extends upward from the bottom portion 111 of the container at least partly upward into said cavity 101, such as in the form of a punt in a wine bottle. In such embodiments the light source 130 is preferably disposed within the inner annulus 118 to irradiate the fluid 1 that is contained within the cavity 101.

The fluid 1 is one of body paint, massage oil, external lubricants, internal lubricants, lotions, creams or moisturizers, face paint, make up and the like. By fluid, we also mean a gel or cream that is relatively viscous, such as Vaseline™, as one example of a brand of petroleum jelly. Such formulations can be conventional but include at least one component having a luminescent property, such as a soluble chemical compound or dispersed phosphorescent, fluorescent or luminescent pigment, such as those disclosed in the aforementioned US patent application number 2008/US20080057089 A1.

A light source 130 is optionally disposed in optical communication with the interior contents of the container 100 through one or more transparent portions, such as the annulus 118, or portion of the sidewall or an upward intruding internal light pipe, or any other internal lighting element. The light source 130 is preferably a light emitting diode (LED) that emits blue light, which is light with wavelengths generally less than about 450 nm. The light source 130 is also preferably energized by an external source which is connected at an external socket connection 125, which is wired to the light source 113, but can also be energized with a battery that is either replaced or re-charged through the socket 125 via a charging circuit, or by a main power source (120 VAC in the US).

FIG. 1A illustrates a first embodiment of such an invention in which the light source 130 and the external socket 125 are contained in a removable base element 120. FIG. 1B illustrates the container 100 separated from the removable base 120 with the cap 115 removed from the rim 130 of the container so the fluid content 1 can be removed and used to dispense the contents remote from the base 120.

The connection to the external socket 125 is preferably of a standard format used for charging mobile phones, smart phones, tablet style computing devices and personal computers and the like. Such as, USB format, micro USB, as well as proprietary formats found on Apple™ brand computer products and Android OS™-based computing products and displays.

In a more preferred embodiment of the invention, the container 100 has one or more transparent inner core member, such as the transparent annulus 118 for receiving a detachable light source 130. The detachable light sources 130 is on a base 120 that includes either a power supply, or an external plug connection to an external power supply. The inner core of the container is transparent to the light emitted by the light source. The detachable light source 130 is optionally firmly attached to the container, such as by a screw, bayonet or snap fitting, so that a user can externally agitate the container contents so that the fluid therein mixes and is uniformly exposed to the light source before the fluid is removed from the container via an upper opening at the rim. The attachment can be via the base 120, or the light source 130 can be part of the container 100, in which case the base 120 also provide an upward facing socket type electrical connection to the battery or charging/power socket of the base.

In various more preferred embodiments, container 100 also has an integrated heater element 140 in thermal communication with the contents of the container. Such heating elements 140 are optionally etched foil resistive heating elements, which can be embed in the container walls or base, but are conventionally embedded in silicone rubber to be placed adjacent to the container 100. Heating elements are also optionally positive temperature coefficient resistive heating elements, thin film heating elements and the like.

Figure 2B:
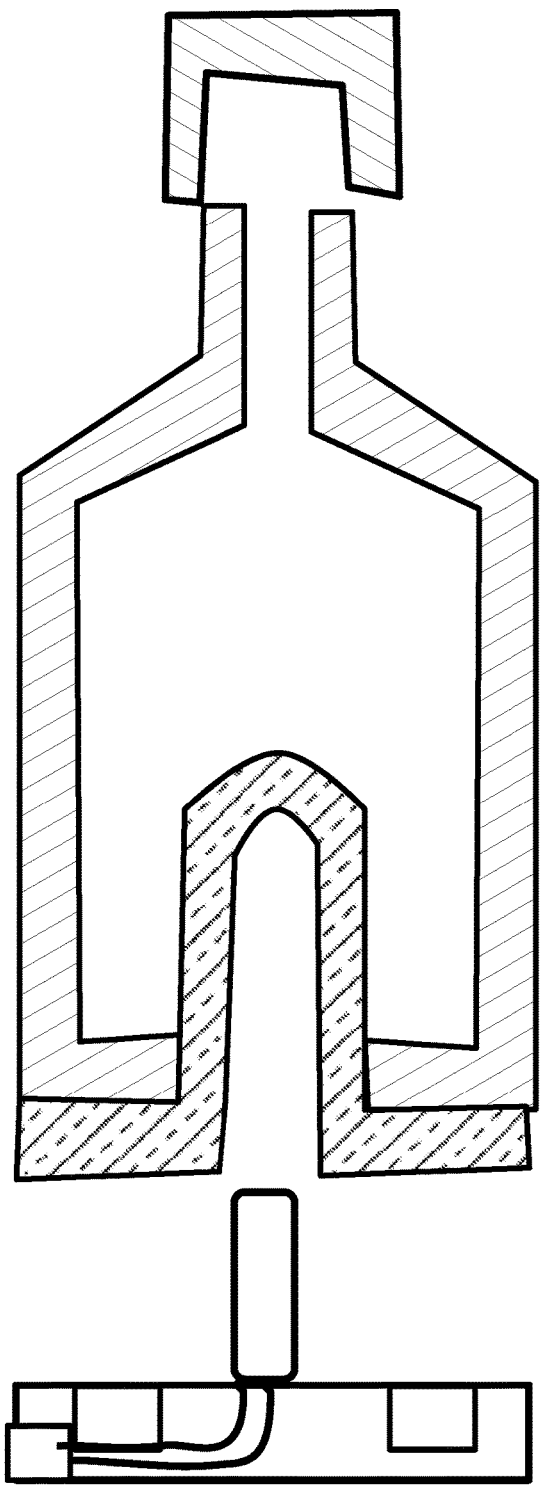
FIG. 2B shows the components thereof separated for a method of use.

FIGS. 2A and 2B similarly illustrate a second embodiment of the invention in which the removable base 120 further comprises an annular heating element 140 disposed around the light source 110 but in thermal communication with the bottom portion 111. The position of the heater element 140 and light source 130 can also be reversed, with the heater in the inner annulus 118 and the light source 130 surrounding it to illuminate a transparent base 111. A plurality of separate light sources can be arranged around the perimeter of the base 120, or around external side walls 112 that are transparent.

FIGS. 3A and 3B similarly illustrate a third embodiment of the invention in which the removable base 120 has heating elements 141 that form an annular wall that surround the lower portion of the container walls 112.

FIGS. 4A and 4B similarly illustrate a fourth embodiment of the invention in which the removable base 120 has a battery 150 disposed therein for powering the light source 130, in which the battery 150 is preferably but not exclusively charged by a external socket connection 125.

It should be appreciated that it is desirable for the container cavity portion 101 between the outer walls and the inner annulus be sufficiently thin with respect to the output of the light source and the extinction coefficient of the fluid with respect to the exciting wavelengths of light for luminescence that sufficient light reaches most of the fluid within the container. However, it is also anticipated that in use a user will lift and shake the container so as to more fully distribute the fluid therein, allowing any portion of the fluid that has not been illuminated to mix and become exposed to light source 130 with additional time.

It may also be desirable that some portion of the container 100 have a exterior transparent window 116 so that a user can extinguish the room lights to determine if the contents are sufficiently charged with light to exhibit phosphorescent or fluorescent properties when the light sources de-energized.

Such an embodiment is illustrated in FIGS. 5A and 5B in which an upper portion of the container is transparent, forming window 116. The embodiment of FIG. 5B also illustrate a mixing blade 501 assembly disposed about the annular portion 118. The mixing portion or mixing blade assembly can be a fixed a series of static mixing blades that are rotated and curves, or blades that rotate when the bottle is agitated, or a blade assembly rotated by an axial connection 502 with the cap, such as via a magnetic coupling so the cap can be removed. Alternatively, the cap 115 can have a secondary dispensing orifice and rotate on the rim 113 to rotate the axial member and stirrer assembly 501/502. Alternatively, the stirring blades can be any shape or types, and are also optionally coupled to base 120, such as with a direct or geared drive shape penetrating the bottom of the container, or with a magnetic stirring assembly. In either case, the base may deploy a motor to rotate the base magnet, which attract the internal stirring bar or assembly the co-rotates to mix the content or drives blades.

A more preferred embodiment is a transparent container, which can be entirely or partially transparent, in which the stirring assembly rotates and translates axially with the bottom. They can be accomplished with a stirring assembly that encounters an internal circular ramp in the interior bottom. An axially bottom penetrating drive shaft can also drive a cyclic vertical translation with simultaneous rotation, provide the stirring assembly can freely translates on it, such as with an internally sealed telescope in the axle. It is anticipated that such an embodiment would also provide a dynamic and decorative glow effect as the luminescent material mixes and translates, the disappearance of mixing striations indicating the luminescent material is fully charged with photonic energy for dispensing at the highest brightness. Any embodiment of the mixing blades may deploy sets or shape or serrated protuberance, such as teeth, that aid in breaking up and dispersing hardened agglomerate of pigment material, which can also be softened by warming with heaters or heat emitting light source.

Figure 9:
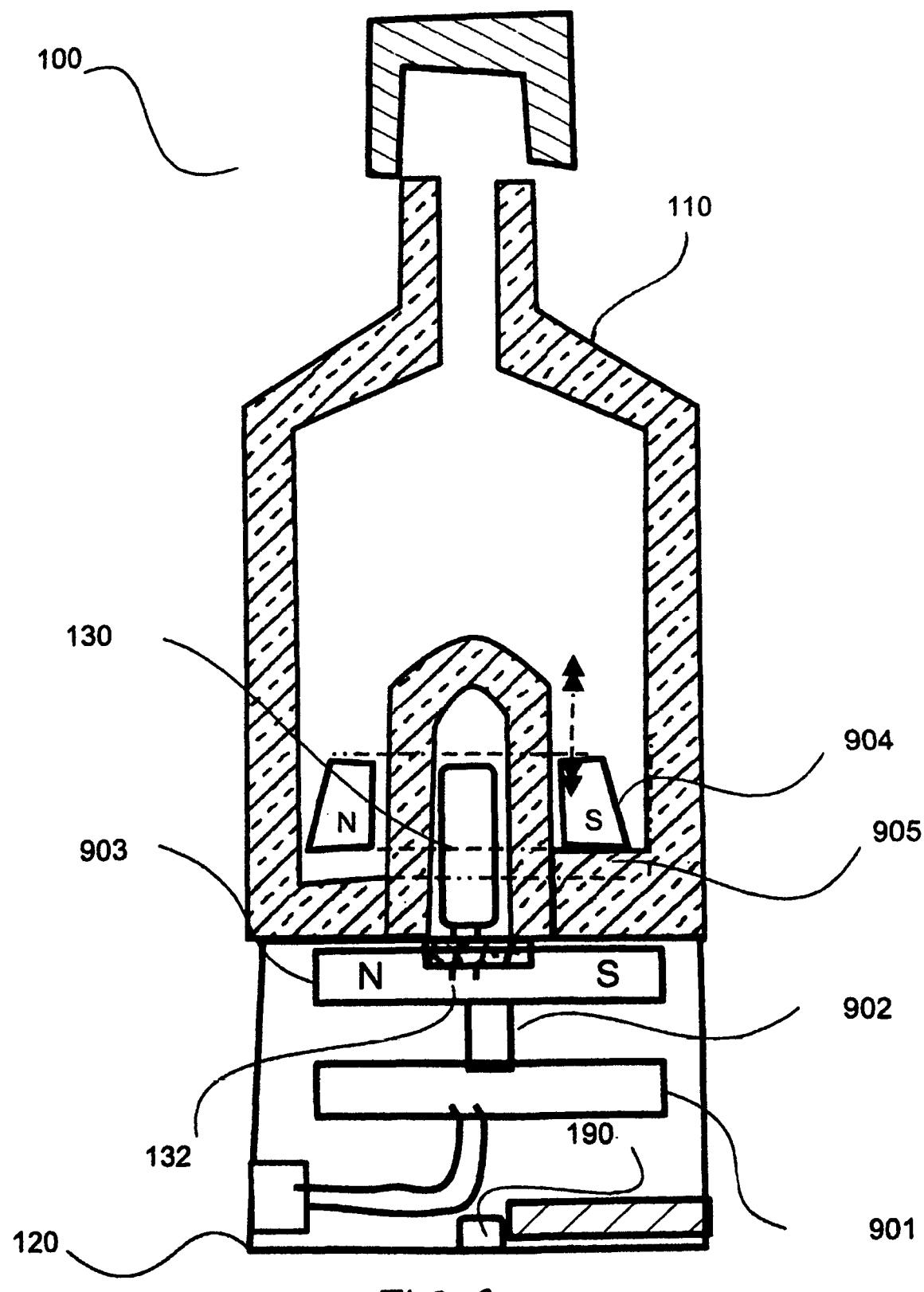
FIG. 9 is a cross-sectional elevation view of another embodiment of the invention.
Figure 10:
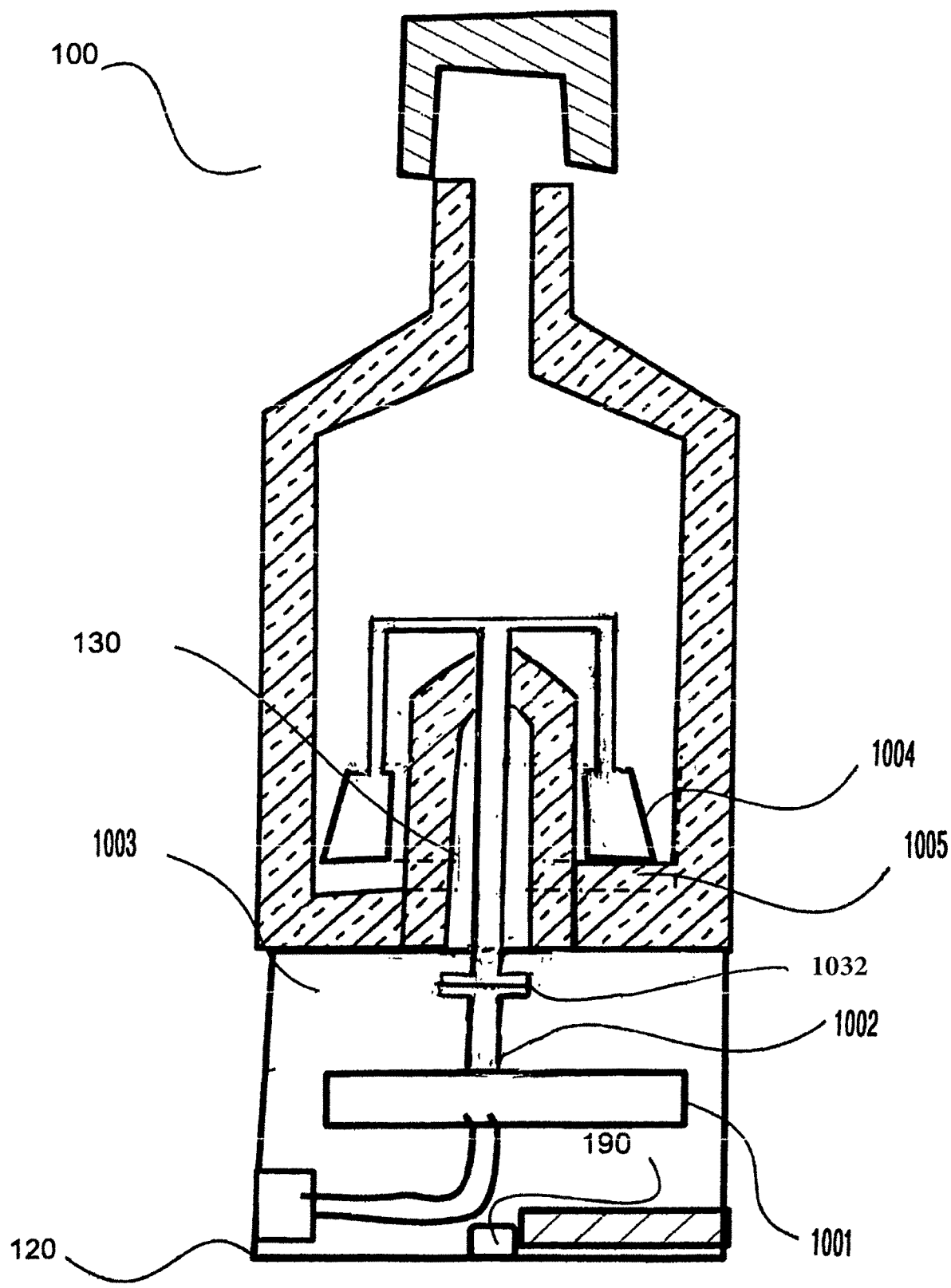
FIG. 10 is a cross section of one embodiment of the present invention wherein a motor drives a shaft with a coupling for turning a mixing blade.

In such embodiments, the annulus can be combined with mixing blades, fins, bar and the like, which extend radially. When such an embodiment is combined with a magnetic drive for the mixing, the light from the light source can illuminate the annulus via a window in the base to avoid penetrating the bottom of the container, which is transparent adjacent container bottom. Alternatively, the blades can use the annulus containing the bulb or light source 130 as a central rotating hub. This embodiment is illustrated in FIG. 9 showing a motor 901 in the base 120, which drives shaft 902 that is connected to a magnetic annular disk or magnet array on a disk 903, in which the light source electrical connection is through the central bore of the annular disk 903. The motor 901 thus rotates the magnet 903 in the base, which rotates the stirrer blade assembly 904 with embedded magnets, shown as N and S for the pole that aligned with the disk magnet 903. The controller 190 optionally controls the motor 901 to conserve battery power when not connected, if desired by the user per the remote programming of portable electronic devices, such as smart phones, and tablet computers. Wiring to the light source 130 can be through an axial bore in the motor, or the motor 901 can be offset from the light connection to drives the shaft 902 or magnet 903 by a gear assembly. It should be appreciated that any battery can be charged by inductive coupling chargers that do not require a wire connection. It should be noted that FIG. 9 also illustrates the axial ramp 905 in section view, the right side of the bottle having a thicker bottom, than the left, so the stirring assembly, having a non-planar bottom, rises as the rotation of the stirrer 904 bottom moves up and down with the ramp 905 shape.

Figure 6:
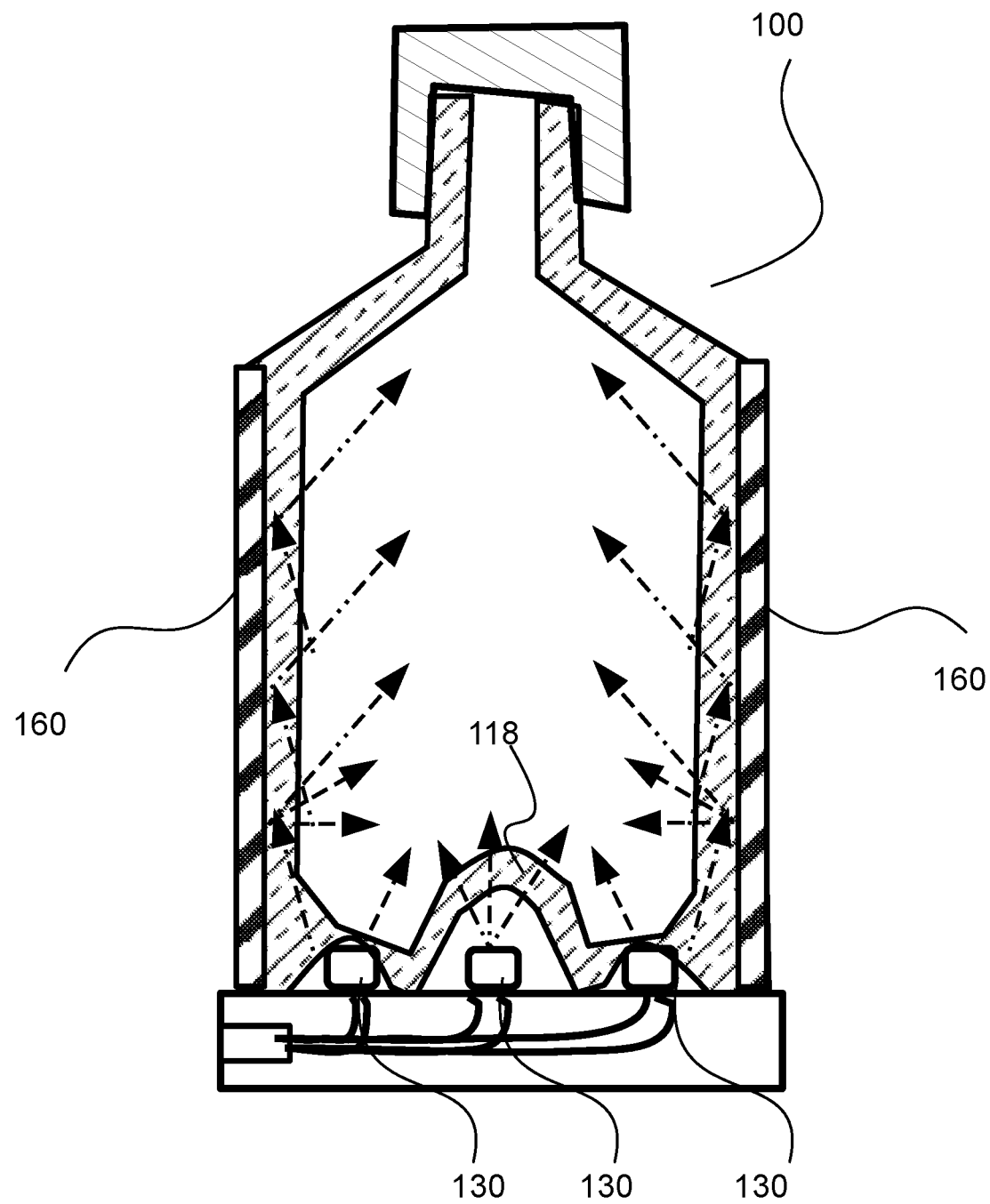
FIG. 6 is a cross-sectional elevation view of another embodiment of the invention.

FIG. 6 illustrates another embodiment of the invention in which the container 110 is transparent and has a metal reflective coating, plating or cladding 160 facing the exterior 112a of the side wall. A plurality of light sources 131 and 132 are disposed around the perimeter of the base 120 to inject light into the transparent side walls 112, as shown by broken line arrows. This light is reflected off the metallic coating and into the interior cavity 101 of the container 110. The base 120 may also include a centrally disposed light source 130, which optionally illuminates or extends into the transparent inner annulus. The container walls 112 can have facets for reflecting the light into the cavity 101 and/or the angular distribution of light into the walls 112 can be shaped by lenses associated with the light sources 130.

Figure 7:
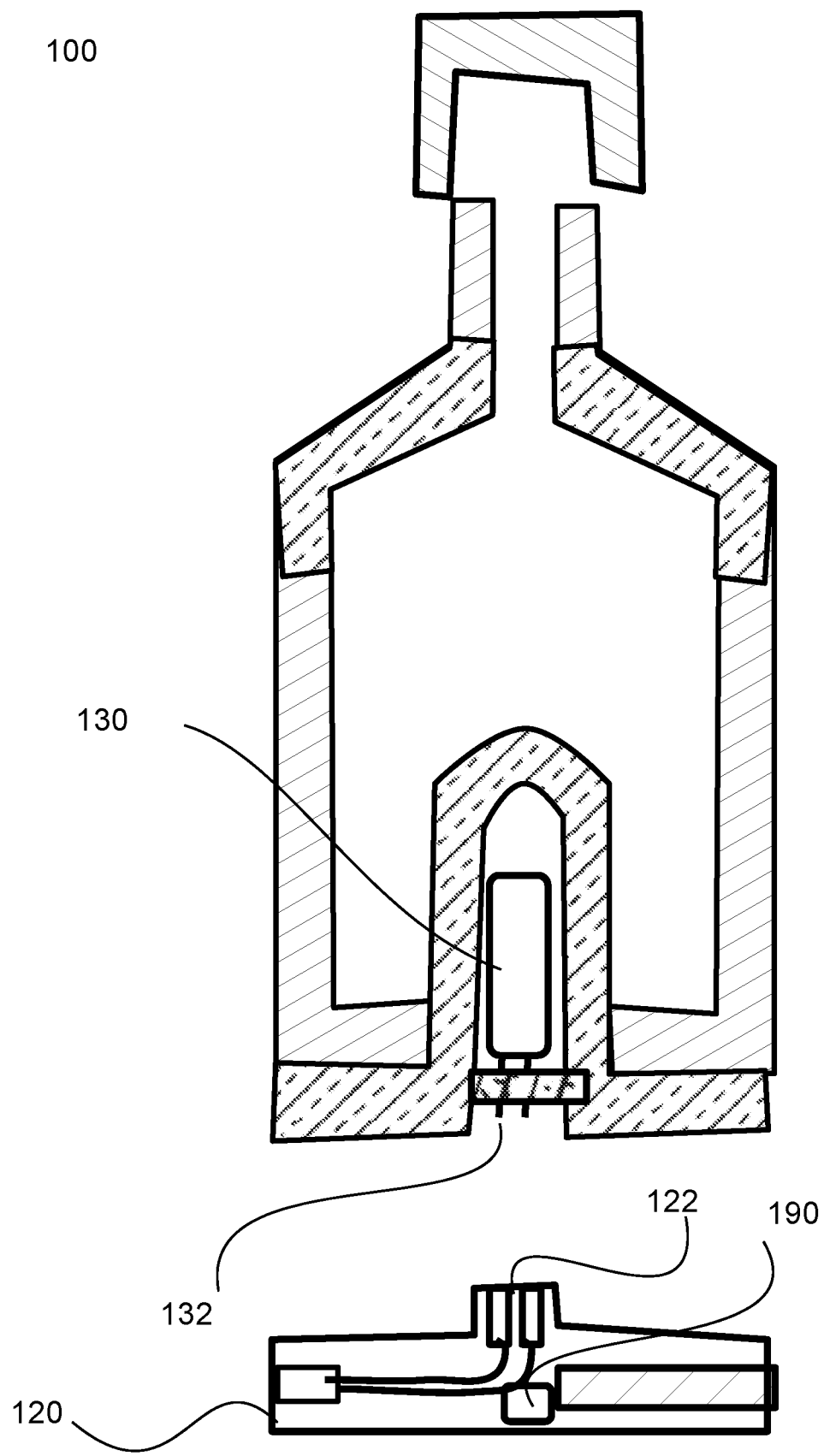
FIG. 7 is a cross-sectional elevation view of another embodiment of the invention.

In the embodiment of FIG. 7, the base 120 includes a controller 190 in signal communication with an external source, such as via a Wi-Fi or Bluetooth™ connection (via a transceiver or transmitter associated with the controller) to energize at least one of the light source and heating/warming elements. Further, such a controller 190 or the external source can signal when the contents are warm, and are fully charged by irradiation to provide the desired illuminant properties when the fluid 1 is ready to dispense, as well as when the contents should be mixed or stirred. The external device is optionally a portable computing device, such as a phone, smart phone or tablet computer and the like. In FIG. 7, the light source is also optionally disposed and fixed in the annular cavity 118, and connects to the base 120 via a mating plug and socket 132 and 122 respectively. The controller 190 may also be in signal communication to activate an external display that is visible at the edge, side or top of the base, such as to display charger status, battery charge state, wireless connection status, temperature, remaining time to charge, remaining time to use, mix, when to shake or otherwise distribute the contents, and the like. Such information can also be transmitted to another device by the controller 190. Further, the transmitter of the controller is also optionally can tuned on/off manually, or can be controlled by the controller via Wi-Fi, Bluetooth™, or cellular phone connection, computer. Further, via a controller the motor and any other hardware or electronic components can be wirelessly activated or energized, or de-activated or de-energized.

Figure 8:
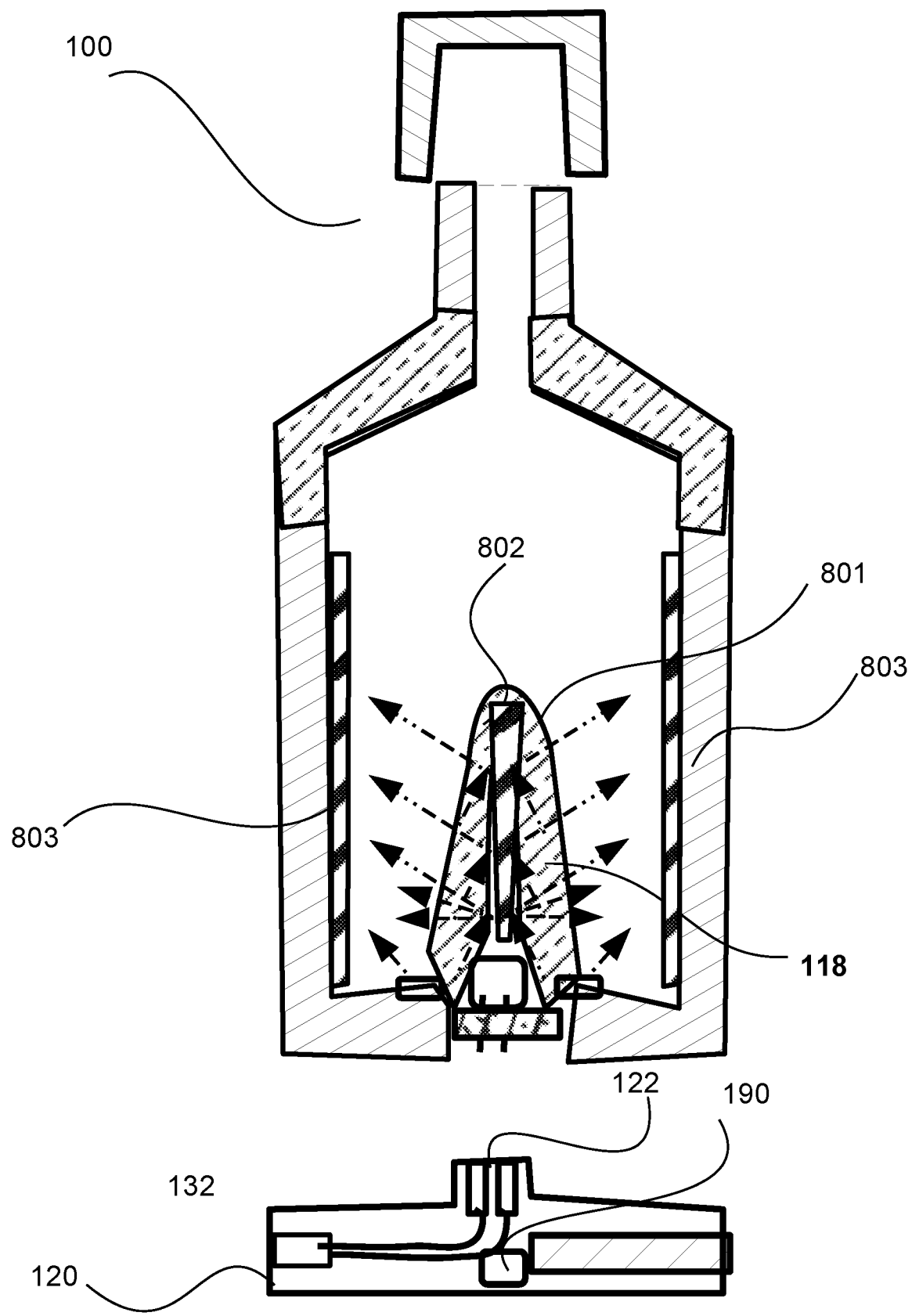
FIG. 8 is a cross-sectional elevation view of another embodiment of the invention.

The embodiment of FIG. 8 deploys a solid annulus or cone 801 that has a reflective metal core 802 such that it acts as a light pipe for the light source in the base. As shown by broken line arrows, light is reflected off the metallic coating or core and into the interior cavity 101 of the container 110. The lower container walls are optionally reflective, having an inner reflective layer 803 or transparent as in FIG. 5 with an outer reflective metallic covering 160. The metal core 802 may have facets to control the dispersion of light broadly into the cavity 101.

An internal or external reflective covering of the container 101 can also function as a thin film heating elements, such as an etched foil heater. The base and controller may also deploy a thermistor, thermocouple or other thermal sensor to prevent overheating the contents and signal from such a sensor indicate the contents have already been warmed to a comfortable temperature or at least a sufficient temperature to re-disperse the luminescent pigment, or lower the fluid 1 viscosity sufficiently to disperse such pigment by one of shaking, stirring and agitating, and the like. Further, the base 120 may container a circuit or micro-switch to detect when the container 110 is removed from base 120, and de-energize the light source 130, and de-energize the heater element(s) 140.

In any of the embodiments, the battery is optionally charged by a photovoltaic source. In any of the embodiments, the lights source can be an LED, incandescent light source, fluorescent light, electroluminescent light and the like. it should be appreciate that an incandescent or other light source can be used both to illuminate and charge the luminescent material, as well as heat the contents. In any of the embodiment, the walls can be rigid or flexible to squeeze the fluid out of a nozzle or opening at the rim or within the cap. The drawings are not intended to represent a particular size or scale, or be construed as limiting in any way. The various illustrations shows cross-sections, as it is contemplated that preferred embodiments will have circular symmetry. However, the container 110 and base 120 need not have exclusivity a cylindrical shape or any particular shape. In any of the embodiments, the base may deploy a plurality of different connector types socket to accept different types of proprietary charger plugs to charge the battery power the heater and or energize the light sources. Further, in any of the embodiment may deploy multiple transparent inner annuluses 118, each illuminating the container cavity by an associated light source and/or the light pipe or cone 801 of FIG. 8, as appropriate to the container size and available output of the light source and the fluids optical properties.

In preferred embodiment the hardware components, such as light source(s), and bulb(s), motor, stirring blades, drive axles, magnets, battery(s), electronic components, and the parts that form the base, can be snapped in or out of mating components to open and replace or remove them from the base for servicing and maintenance of the device 100.

Another aspect of the invention is providing a means to replace the fluid 1 when the container 110 is empty or nearly empty. The container can be refilled by mixing a fluid base, such as a silicone fluid and a powered fluorescent pigment from separate container or pre-measured sealed packet. Such packets can be provided of pigments that fluoresce in different colors, and are preferably alkaline earth aluminates, such as without limitation are strontium aluminate, silicate aluminate, or any alkaline earth aluminate. A number of earth metals can be used depending on the particular product and color desired, including strontium, magnesium, calcium, and barium, to make, for example, barium aluminate, calcium aluminate, and magnesium aluminate. The glowing colors span the spectrum from greenish yellow to purple blue. Silicon or titanium may be added, and each alkaline earth metal aluminate may be doped with europium or other rare earth elements. Further, alkaline earth silicates can be employed, as can silicate aluminate and zinc sulfide, though with notably less luminosity and persistence than strontium aluminate. Alkaline earth silicate produces a sky blue color not produced by alkaline earth aluminates. Yet another alternative is earth mineral crystals.

While the invention has been described in connection with a preferred embodiment, it is not intended to limit the scope of the invention to the particular form set forth, but on the contrary, it is intended to cover such alternatives, modifications, and equivalents as may be within the spirit and scope of the invention as defined by the appended claims. More particularly, it should be understood that the disclosure of a particular features, aspect or variant with respect to one embodiment is not intended to preclude combinations or exclusions of such features, aspects or variants from others embodiments.

I claim:

1. A fluid dispenser comprising:
   a) a container having a bottom portion and an upper portion, said bottom portion surrounded by a substantially upright sidewall which extends upward to said upper portion terminating with a cap removably connected thereto, wherein said upper portion and said bottom portion of the container and said sidewall define a cavity for confining and dispensing a fluid, wherein the fluid dispenser further comprises the fluid having dispersed or dissolved luminescent material therein at least partially filling the container and wherein the sidewall of the container is deformable to squeeze the fluid from the container,
   b) a transparent inner annulus that extends upward from the bottom portion of the container at least partly upward into said cavity wherein a mixing blade assembly within the container is disposed about the transparent inner annulus,
   c) an illuminating base, said illuminating base further comprising an external socket for receiving a power connection, and a motor wherein the motor drives a magnet in the illuminating base which is magnetically coupled to a magnet in the mixing blade assembly, d) a light source wherein the light source is a light emitting diode (LED) said light emitting diode emitting blue light when illuminated, e) a means to connect the illuminating base to the bottom of the container, wherein the external socket is wired to said light source, said illuminating base removably attachable to the bottom of the container with a snap, bayonet or screwed fitting so as to dispose said light source in optical communication within the inner annulus to irradiate contents within the cavity.

2. A fluid dispenser comprising:

a) a container having a bottom portion and an upper portion, said bottom portion surrounded by a substantially upright sidewall which extends upward to said upper portion terminating with a cap removably connected thereto, wherein said upper portion and said bottom portion of the container and said sidewall define a cavity for confining and dispensing a fluid, wherein the fluid dispenser further comprises the fluid having dispersed or dissolved luminescent material therein at least partially filling the container and wherein the sidewall of the container is deformable to squeeze the fluid from the container, b) a transparent inner annulus that extends upward from the bottom portion of the container at least partly upward into said cavity wherein a mixing blade assembly within the container is disposed about the transparent inner annulus, c) an illuminating base, said illuminating base further comprising an external socket for receiving a power connection, and a motor wherein said motor drives a shaft that penetrates the container bottom portion said shaft having a mechanical coupling to the mixing blade assembly, d) a light source wherein the light source is a light emitting diode (LED) said light emitting diode emitting blue light when illuminated, e) a means to connect the illuminating base to the bottom of the container, wherein the external socket is wired to said light source, said illuminating base removably attachable to the bottom of the container with a snap, bayonet or screwed fitting so as to dispose said light source in optical communication within the inner annulus to irradiate contents within the cavity.

* * * * *